United States Patent
Kusaba

(10) Patent No.: US 12,311,073 B2
(45) Date of Patent: May 27, 2025

(54) HYGIENE EVALUATING DEVICE, HYGIENE EVALUATION IMAGING SYSTEM, IMAGING STAND, AND HYGIENE EVALUATION METHOD

(71) Applicant: Moraine Corporation, Tokyo (JP)

(72) Inventor: Tsuneki Kusaba, Tokyo (JP)

(73) Assignee: Moraine Corporation, Tokyo (JP)

( * ) Notice: Subject to any disclaimer, the term of this patent is extended or adjusted under 35 U.S.C. 154(b) by 722 days.

(21) Appl. No.: 17/299,846

(22) PCT Filed: Dec. 5, 2018

(86) PCT No.: PCT/JP2018/044673
§ 371 (c)(1),
(2) Date: Aug. 9, 2022

(87) PCT Pub. No.: WO2020/115832
PCT Pub. Date: Jun. 11, 2020

(65) Prior Publication Data
US 2022/0370674 A1  Nov. 24, 2022

(51) Int. Cl.
*A61L 2/28* (2006.01)
*G06T 7/00* (2017.01)

(52) U.S. Cl.
CPC .............. *A61L 2/28* (2013.01); *G06T 7/0012* (2013.01); *G06T 2207/30088* (2013.01)

(58) Field of Classification Search
CPC .......... A61L 2/28; G16H 15/00; G16H 40/20; G16H 40/63; G16H 40/67; G06T 2207/30088; G06T 7/0012; Y02A 40/81
See application file for complete search history.

(56) References Cited

U.S. PATENT DOCUMENTS 9,424,735 B2    8/2016  Haidegger et al.
9,870,716 B1 *  1/2018  Rao .................... H04N 21/2353
(Continued)

FOREIGN PATENT DOCUMENTS

JP    2001282931 A    10/2001
JP    2009282442 A    12/2009
(Continued)

OTHER PUBLICATIONS

Neil Deochand et al.,"Brief Report on Hand-Hygiene Monitoring Systems: A Pilot Study of a Computer-Assisted Image," Jun. 2016, Journal of Environmental Health , vol. 78, No. 10 (Jun. 2016), pp. 14-17.*

(Continued)

*Primary Examiner* — Omar S Ismail
(74) *Attorney, Agent, or Firm* — Troutman Pepper Locke LLP

(57) ABSTRACT

Provided is a hygiene evaluation apparatus capable of precisely evaluating a hygiene state of hands. A hygiene evaluation apparatus includes a captured image acquiring unit that acquires a captured image of a hand, a calculating unit that calculates a score regarding a substance stuck to the hand, using the captured image, and an output unit that outputs the score calculated by the calculating unit. It is possible to more precisely perform evaluation by more directly evaluating a hygiene state of hands using the captured image of the hands.

13 Claims, 13 Drawing Sheets

(56) References Cited

U.S. PATENT DOCUMENTS

| | | | |
|---|---|---|---|
| 2002/0070970 A1* | 6/2002 | Wood | G06T 7/0012 |
| | | | 715/766 |
| 2003/0095697 A1* | 5/2003 | Wood | G06V 10/25 |
| | | | 382/154 |
| 2008/0074055 A1* | 3/2008 | Peterson | H05B 41/32 |
| | | | 315/241 P |
| 2008/0303658 A1 | 12/2008 | Melker et al. | |
| 2010/0121201 A1* | 5/2010 | Papaioannou | A61B 5/0064 |
| | | | 382/128 |
| 2011/0297696 A1 | 12/2011 | Casares | |
| 2013/0109915 A1* | 5/2013 | Krupnik | G06F 3/04845 |
| | | | 600/109 |
| 2013/0197371 A1* | 8/2013 | Chiba | A61B 1/0646 |
| | | | 600/407 |
| 2014/0336516 A1* | 11/2014 | Rizzo | A61B 5/4842 |
| | | | 600/476 |
| 2015/0230712 A1* | 8/2015 | Aarabi | A61B 5/0077 |
| | | | 600/476 |
| 2015/0366456 A1* | 12/2015 | Takamori | A61B 5/0077 |
| | | | 600/479 |
| 2016/0120437 A1* | 5/2016 | Graham | A61B 5/16 |
| | | | 600/411 |
| 2017/0270350 A1* | 9/2017 | Maltz | A61B 5/7275 |
| 2017/0272741 A1* | 9/2017 | Maltz | G06K 7/1417 |
| 2018/0321153 A1 | 11/2018 | Llamido | |
| 2019/0172336 A1* | 6/2019 | Haidegger | A61L 2/28 |
| 2019/0311191 A1* | 10/2019 | Aarabi | G06V 10/443 |
| 2020/0113438 A1* | 4/2020 | Bourquin | A61B 5/448 |
| 2020/0118164 A1* | 4/2020 | DeFrank | G06Q 30/0269 |
| 2020/0250825 A1* | 8/2020 | Breslavets | G06T 7/0014 |
| 2021/0110700 A1* | 4/2021 | Harman | G06N 20/00 |
| 2022/0236577 A1* | 7/2022 | Bagneris | G06F 3/011 |

FOREIGN PATENT DOCUMENTS

| | | |
|---|---|---|
| JP | 5097965 B2 | 12/2012 |
| JP | 3184482 U | 6/2013 |
| JP | 2014-52976 A | 3/2014 |
| JP | 3209337 U | 3/2017 |
| JP | 2016-186438 A | 10/2018 |
| WO | 2012042285 A1 | 4/2012 |
| WO | 2018109507 A1 | 6/2018 |

OTHER PUBLICATIONS

Noguchi, "Teaching System of Foot Cleaning Self-care for Prevention of Tinea Pedis in Diabetic Patients", The Japan Society of Mechanical Engineers; No. 15-2 Proceedings of the 2015 JSME Conference on Robotics and Mechatronics, Kyoto, Japan, May 17-19, 2015.
https://web.archive.org/web/20170814025852/http://pro.saraya.com:80/tearaicheker/(Web page & Slide).
https://pt.slideshare.net/FerenceNagy7/semmelweis-hygiene--scanner--to-prevent-hai-infections.
International Search Report issued in corresponding International Application No. PCT/JP2018/044673 dated Feb. 5, 2019, with English translation.
First Office Action & English translation dated Jan. 15, 2024, from corresponding Chinese Application No. 201880100018.5.
Extended European search report EP18942414.6 dated Jun. 10, 2022.

* cited by examiner

| User identifier | Time and date information | Score |
|---|---|---|
| U001 | 9:15, July 3, 2017 | 6 |
| U001 | 9:08, July 4, 2017 | 4 |
| ⋮ | ⋮ | ⋮ |
| U002 | 9:25, July 3, 2017 | 12 |
| U002 | 9:02, July 4, 2017 | 9 |
| ⋮ | ⋮ | ⋮ |
| U003 | 9:19, July 3, 2017 | 13 |
| U003 | 9:07, July 4, 2017 | 15 |
| ⋮ | ⋮ | ⋮ |

FIG.5

Hygiene evaluation image capturing system 5

HYGIENE EVALUATING DEVICE, HYGIENE EVALUATION IMAGING SYSTEM, IMAGING STAND, AND HYGIENE EVALUATION METHOD

CROSS REFERENCE TO RELATED APPLICATION

This is a U.S. National Phase application under 35 U.S.C. § 371 of International Patent Application No. PCT/JP2018/044673, filed Dec. 5, 2018. The entire content of this application is hereby incorporated by reference.

TECHNICAL FIELD

The present invention relates to a hygiene evaluation apparatus and the like for acquiring an image of a hand, and calculating a score regarding a substance stuck to the hand.

BACKGROUND

In order to prevent infection, it is essential to wash hands and to sanitize hands. Accordingly, apparatuses for evaluating a hygiene behavior regarding hands and fingers have been conventionally developed in order to evaluate whether or not such a hygiene behavior has been properly performed (see JP 2009-282442, for example). With such apparatuses, it is possible to evaluate whether or not an examinee has properly performed handwashing, for example.

SUMMARY

As in the above-described conventional examples, it is possible to evaluate a hygiene state of hands and fingers, by evaluating whether or not a hygiene behavior such as handwashing has been properly performed, but this evaluation is indirect evaluation, and thus the level of precision thereof may be relatively low. The reason for this is that, for example, there are cases in which dirt between fingers or the like has not been properly removed even when handwashing has been performed.

The present invention was made in order to address the above-described problem, and it is an object thereof to provide a hygiene evaluation apparatus and the like capable of more precisely evaluating a hygiene state of hands.

In order to achieve the above-described object, the present invention is directed to a hygiene evaluation apparatus including: a captured image acquiring unit that acquires a captured image of a hand; a calculating unit that calculates a score regarding a substance stuck to the hand, using the captured image; and an output unit that outputs the score calculated by the calculating unit.

With this configuration, it is possible to more directly evaluate a hygiene state of a hand, by calculating a score regarding a substance stuck to the hand (e.g., a substance remaining in a portion in which handwashing has not been properly performed, a substance that is present in a portion into which a sanitizer has been properly rubbed, etc.), using a captured image of the hand. As a result, it is possible to more precisely perform evaluation.

Furthermore, in the hygiene evaluation apparatus according to the present invention, it is also possible that the calculating unit calculates the score, using a proportion of an area of a region to which a substance is stuck with respect to an area of the hand.

With this configuration, it is easy to evaluate whether or not the hygiene state of the entire hand is good.

Furthermore, in the hygiene evaluation apparatus according to the present invention, it is also possible that the calculating unit calculates the score, according to whether or not a substance is stuck to predetermined portions of the hand.

With this configuration, for example, it is possible to more properly evaluate the hygiene state from the viewpoint of preventing infection, by setting proper portions for the tips of fingers and the like at which it is important to improve the hygiene state.

Furthermore, in the hygiene evaluation apparatus according to the present invention, it is also possible that the score is a value regarding a degree to which a substance that has not been removed through handwashing remains on the hand.

With this configuration, for example, it is possible to evaluate whether or not a substance rubbed into a hand before handwashing has been properly removed through handwashing, that is, whether or not proper handwashing has been performed.

Furthermore, in the hygiene evaluation apparatus according to the present invention, it is also possible that the score is a value regarding a degree to which a substance contained in a sanitizer is stuck to the hand.

With this configuration, for example, it is possible to evaluate whether or not a sanitizer has been properly rubbed into the entire hand.

Furthermore, in the hygiene evaluation apparatus according to the present invention, it is also possible that the hygiene evaluation apparatus further includes an accepting unit that accepts a user identifier for identifying a user subjected to image capturing, wherein the output unit outputs the score and the user identifier accepted by the accepting unit in association with each other.

With this configuration, it is possible to manage the score for each user.

Furthermore, in the hygiene evaluation apparatus according to the present invention, it is also possible that the hygiene evaluation apparatus further includes a time and date information acquiring unit that acquires time and date information indicating a time and date at which the captured image was captured, wherein the output unit outputs the score, the user identifier, and the time and date information acquired by the time and date information acquiring unit, in association with each other.

With this configuration, it is possible to manage the score for each user, for each point in time and date. Accordingly, for example, it is also possible to see whether or not a hygiene state of a hand of a user has been improved, using the result.

Furthermore, in the hygiene evaluation apparatus according to the present invention, it is also possible that the hygiene evaluation apparatus further includes: an accepting unit that accepts a user identifier for identifying a user subjected to image capturing; and a statistical processing unit that performs statistical processing on scores respectively corresponding to multiple users identified with multiple user identifiers accepted by the accepting unit, wherein the output unit outputs a result of the statistical processing as well.

With this configuration, for example, it is possible to output a result of the statistical processing such as an average of scores of multiple users.

Also, the present invention is further directed to an image capturing mount including: a mount on which the hygiene evaluation apparatus is detachably mounted; and a light source provided on the mount, wherein the captured image acquiring unit acquires the captured image, by capturing an image of a hand irradiated with light from the light source.

With this configuration, it is possible to evaluate a hygiene state of a hand, using the image capturing mount. For example, it is possible to evaluate a hygiene state of a hand, by mounting a hygiene evaluation apparatus that is a portable information terminal such as a smartphone on the image capturing mount.

Furthermore, in the image capturing mount according to the present invention, it is also possible that the mount includes a stage portion on which the hygiene evaluation apparatus is mounted, and a leg portion attached to the stage portion, and a hand image capturing space defined by the stage portion and the leg portion has a size that allows the captured image acquiring unit to capture images of both hands simultaneously.

With this configuration, images of both hands can be simultaneously captured, and thus it is possible to more efficiently perform evaluation compared with the case in which an image of one hand is captured at a time.

Furthermore, in the image capturing mount according to the present invention, it is also possible that the leg portion is foldably attached to the stage portion.

With this configuration, for example, it is possible to provide an image capturing mount that is excellent in terms of portability and accommodatability.

Also, the present invention is further directed to a hygiene evaluation image capturing system including: the image capturing mount; and the hygiene evaluation apparatus mounted on the mount.

Also, the present invention is further directed to a hygiene evaluation method including: a captured image acquiring step of acquiring a captured image of a hand; a calculating step of calculating a score regarding a substance stuck to the hand, using the captured image; and an output step of outputting the score calculated in the calculating step.

With the hygiene evaluation apparatus and the like according to the present invention, it is possible to more directly evaluate a hygiene state of a hand, by calculating a score regarding a substance stuck to the hand, using a captured image of the hand, as a result of which it is possible to more precisely perform evaluation.

BRIEF DESCRIPTION OF DRAWINGS

FIG. 5 is a table showing an example of the correspondence between a user identifier, time and date information, and a score according to the embodiment.

DETAILED DESCRIPTION

Figure 1:
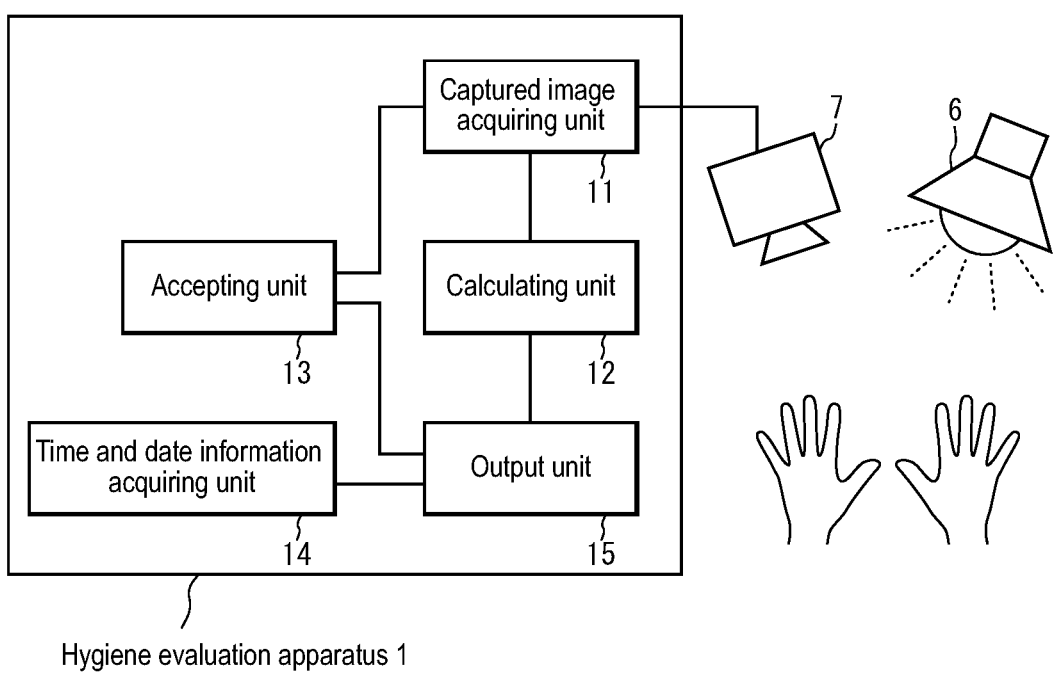
FIG. 1 is a block diagram showing the configuration of a hygiene evaluation apparatus according to Embodiment 1 of the present invention.

Hereinafter, a hygiene evaluation apparatus according to the present invention will be described by way of embodiments. It should be noted that constituent elements and steps denoted by the same reference numerals in the embodiments below are the same or corresponding constituent elements and steps, and thus a description thereof may not be repeated.

Example 1

Hereinafter, a hygiene evaluation apparatus according to Example 1 of the present invention will be described with reference to the drawings. The hygiene evaluation apparatus according to this embodiment acquires an image of a hand, and calculates a score regarding a substance stuck to the hand. It is possible to see a hygiene state of the hand, using the score.

FIG. 1 is a block diagram showing the configuration of a hygiene evaluation apparatus 1 according to this embodiment. The hygiene evaluation apparatus 1 according to this embodiment includes a captured image acquiring unit 11, a calculating unit 12, an accepting unit 13, a time and date information acquiring unit 14, and an output unit 15. The hygiene evaluation apparatus 1 may be a dedicated apparatus for hygiene evaluation of a hand, or a general-purpose information processing apparatus that is used for hygiene evaluation of a hand. In Embodiment 3, the case of the latter, that is, the case in which a hygiene evaluation apparatus that is a portable information terminal such as a smartphone is used for hygiene evaluation of a hand will be described.

The captured image acquiring unit 11 acquires a captured image of a hand. The captured image acquiring unit 11 may acquire a captured image by capturing an image of a hand, or receive a captured image of a hand captured by an image capturing apparatus 7. In this embodiment, the case of the latter will be mainly described. The captured image is typically a still image. In the case in which a moving image is captured by the image capturing apparatus 7, one frame contained in the moving image may be the captured image. The hand subjected to image capturing may be both hands or one hand. The hand subjected to image capturing may be the palm side, the back side, or both sides. From the viewpoint of evaluating the entire hand, it is preferable to capture an image of both sides (the palm side and the back side) of both hands of an examinee. The captured image of both sides of both hands of an examinee may be multiple captured images (e.g., two captured images, four captured images, etc.). The captured image acquired by the captured image acquiring unit 11 may be stored in an unshown storage medium. There is no limitation on the point in time at which the captured image acquiring unit 11 acquires the captured image. For example, it is also possible that, when the accepting unit 13 accepts an instruction to acquire a captured image, the captured image acquiring unit 11 acquires a captured image. It is also possible that, when the image capturing region of the image capturing apparatus 7 includes a hand, that is, when an examinee puts his or her hand into the image capturing region of the image capturing apparatus 7, the captured image acquiring unit 11 acquires a captured image. In this case, the captured image acquiring unit 11 may acquire a captured image satisfying a predetermined condition, out of successively received captured images, as a captured image for use in the following processing. The condition may be, for example, that a hand is detected through pattern matching or the like.

Hereinafter, a hand subjected to image capturing will be described regarding the case (1) in which handwashing is evaluated and the case (2) in which hand sanitization is evaluated.

Case (1) in which Handwashing is Evaluated

An examinee rubs a specific substance into his or her entire hand before handwashing. The specific substance may be a substance that reflects light (e.g., ultraviolet light, etc.) with a wavelength other than that of visible light. In this embodiment, the case in which the specific substance is a fluorescent substance will be mainly described. The fluorescent substance may be a substance that emits light when being irradiated with ultraviolet light. After rubbing the specific substance into the hand, the examinee washes the hand as usual using a soap or the like. Then, the image capturing apparatus 7 captures an image of the hand after the handwashing. The image is preferably captured in a state in which light for facilitating detection of the specific substance stuck to the hand is emitted from a light source 6. The reason for this is that, with this configuration, it is easier to determine whether or not the specific substance is stuck to the hand in the captured image. In the case in which the specific substance is a fluorescent substance, the light source 6 may emit ultraviolet light. The light source 6 that emits ultraviolet light may be, for example, a black light device, an ultraviolet light lamp, an ultraviolet light LED, or other light sources that emit ultraviolet light. In this embodiment, the case in which the light source 6 is a black light device will be mainly described. In the case of (1), a less degree to which a specific substance remains on the hand means that handwashing was performed more properly, that is, a better hygiene state has been obtained.

Case (2) in which Hand Sanitization is Evaluated

An examinee rubs a sanitizer containing a specific substance into his or her entire hand. Then, the image capturing apparatus 7 captures an image of the hand after the sanitization. The image is preferably captured in a state in which light for facilitating detection of the specific substance stuck to the hand is emitted from the light source 6 as with (1). The specific substance and the light source 6 are as described in (1) above. In the case of (2), a more degree to which a specific substance remains on the hand means that sanitization was performed more properly, that is, a better hygiene state has been obtained.

In (1) and (2) above, it is preferable that the specific substance is not visible in light with a wavelength of a visible light region. The reason for this is to prevent patients and the like from feeling that something is amiss in the case in which an examinee is a healthcare worker, for example. Meanwhile, in the case of performing evaluation for training of handwashing, sanitization, and the like, for example, it is also possible that the specific substance is visible in light with a wavelength of a visible light region. In that case, for example, the light source 6 may emit visible light. The specific substance may be, for example, merely a pigment, or may be a substance that is colored upon reacting with dirt, bacteria, or the like. In the case of the latter, the color after the coloring may be visible in visible light.

The calculating unit 12 calculates a score regarding the substance stuck to the hand, using the captured image. The substance is the above-described specific substance. The score may be, for example, a score that increases in accordance with an increase in the degree to which a substance is stuck to the hand, or a score that increases in accordance with a decrease in the degree to which a substance is stuck to the hand. In the case of (1) above, the score is a value regarding a degree to which a substance that has not been removed through handwashing remains on the hand. In that case, a score indicating a less degree to which a substance is stuck to the hand means a better hygiene state. The reason for this is that a less degree to which a substance is stuck to the hand means a smaller amount of substance remaining without being removed through handwashing. In the case of (2) above, the score is a value regarding a degree to which a substance contained in a sanitizer is stuck to the hand. In that case, a score indicating a more degree to which a substance is stuck to the hand means a better hygiene state. The reason for this is that a more degree to which a substance is stuck to the hand means a smaller region into which the sanitizer has not been rubbed.

For example, the calculating unit 12 may calculate the score, using a proportion of an area of a region to which the substance is stuck with respect to an area of the hand. More specifically, the calculating unit 12 may calculate the score, by specifying the area of a region to which the substance is stuck, and dividing the area by the area of the hand. In this case, the score may be, for example, a real number from 0 to 1. For example, the calculating unit 12 may calculate the area of the hand, by detecting the region of the hand in the captured image through contour detection, skin color detection, pattern matching, or the like, and calculating the area of the region. The calculating unit 12 may distinguish a part to which the substance is stuck from a part to which the substance is not stuck in the captured image, by comparing one or more values of the luminance, the lightness, the hue, the saturation, and the like, and a predetermined threshold. The parts may be distinguished from each other, for example, for each pixel of the captured image, or for each set of multiple pixels that are arranged adjacent to each other (e.g., four pixels arranged in 2×2, nine pixels arranged in 3×3, etc.). In the case of distinguishing a part to which the substance is stuck from a part to which the substance is not stuck for each set of multiple pixels that are arranged adjacent to each other, for example, it is possible to determine that the substance is stuck to multiple pixels if the substance is stuck to pixels in a number at a threshold or greater, among the multiple pixels. The threshold may be, for example, the number of pixels that is half the number of multiple pixels that are arranged adjacent to each other, or another number of pixels. In the case of distinguishing a part to which the substance is stuck from a part to which the substance is not stuck for each set of multiple pixels that are arranged adjacent to each other, for example, it is possible to determine whether or not the substance is stuck to the multiple pixels, by comparing an average of one or more of the luminance, the lightness, the hue, the saturation, and the like of the multiple pixels, and a threshold.

Figure 3:
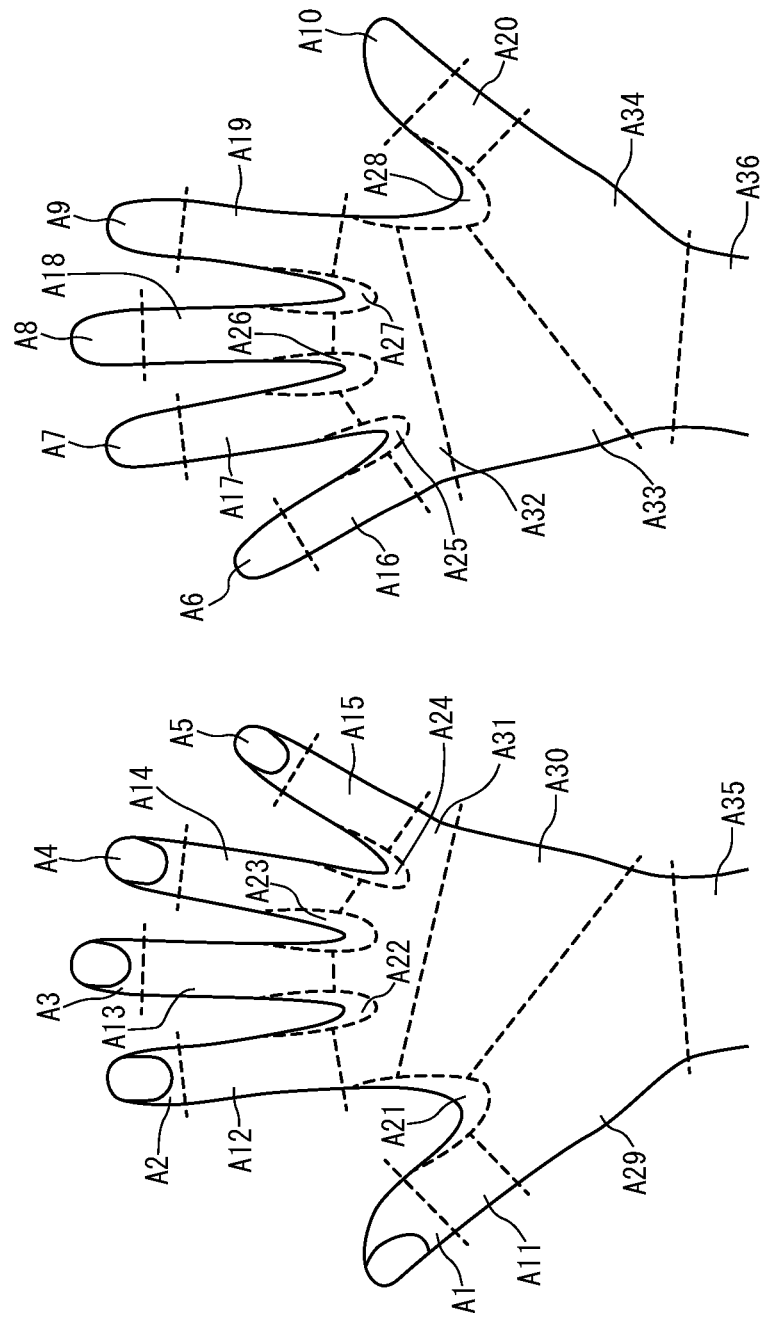
FIG. 3 is a diagram illustrating portions of a hand according to the embodiment.

Furthermore, for example, the calculating unit 12 may calculate the score, according to whether or not the substance is stuck to predetermined portions of the hand. The score may be, for example, the number of portions to which the substance is stuck, or the number of portions to which the substance is not stuck. The portions of a hand may be determined in advance, for example, as shown in FIG. 3. In FIG. 3, the two sides of a right hand are divided into 36 portions of A1 to A36. In a similar manner, the two sides of a left hand may also be divided into 36 portions of A37 to A72. When determining portions, it is also possible to determine the portions such that a portion in which it is important to improve the hygiene state (e.g., the tips of fingers, points between fingers, etc.) has a small area and a portion in which it is not important to improve the hygiene state has a large area. With this configuration, in the scores, the weight of a portion in which it is important to improve the hygiene state can be increased, and it is possible to evaluate whether or not an important portion is in a proper hygiene state. In the case in which the weights according to the portions are set, the calculating unit 12 may calculate the score, by performing weighted addition. For example, the weights may be set such that a portion such as the tips of fingers in which it is important to improve the hygiene state has a greater influence on the score. The calculating unit 12 may determine whether or not the substance is stuck to a portion, for example, by comparing a proportion of an area of a region to which the substance is stuck with respect to an area of the portion, and a threshold (e.g., 50%, 60%, etc.). For example, as for a portion in which the substance is stuck to a region at a proportion at a threshold or greater, the calculating unit 12 may determine that the substance is stuck to that portion.

Hereinafter, the way the calculating unit 12 specifies regions corresponding to predetermined multiple portions (e.g., the portions of A1 to A36 shown in FIG. 3, etc.) in a hand image contained in a captured image will be briefly described. For example, the calculating unit 12 may specify regions corresponding to predetermined multiple portions, in a hand image, by extracting a contour of a hand image contained in a captured image, converting the shape of a hand in which portions are determined in advance as in FIG. 3 or the like, so as to match the extracted contour of the hand, and performing the specification based on the positions of boundaries after the conversion (e.g., the positions of the broken lines shown in FIG. 3). In the case in which the predetermined multiple portions are determined using feature points, the calculating unit 12 may specify regions corresponding to predetermined multiple portions, by extracting the feature points in a hand image contained in a captured image, and performing the specification using the extracted feature points. In the case in which the predetermined portions are determined, for example, as regions corresponding to 20% of the tips of the fingers or regions corresponding to 80% of the bases of the fingers, the calculating unit 12 may specify the regions of the fingers through pattern matching or the like, and specify the predetermined regions, out of these regions. The proportion such as 20% may be a proportion regarding the area. The calculating unit 12 may specify regions corresponding to predetermined multiple portions, in a hand image contained in a captured image, using other methods.

The accepting unit 13 accepts a user identifier for identifying a user subjected to image capturing. The user subjected to image capturing is, in the strict sense, a user having a hand subjected to image capturing. The user is an examinee. It is preferable that a user identifier is accepted such that the correspondence between the user identifier accepted by the accepting unit 13 and a captured image is known. For example, a user identifier and a captured image may be associated with each other, by accepting a user identifier, and then capturing an image of a hand of a user identified with the user identifier. For example, the accepting unit 13 may accept a user identifier, by accepting selection of one user identifier from among multiple user identifiers. In the case in which only one user uses the hygiene evaluation apparatus 1, for example, the accepting unit 13 may accept a user identifier, by reading the user identifier stored in an unshown storage medium. The user identifier may be, for example, a name of a user, a telephone number of a user, or other types of information with which a user can be identified. The accepting unit 13 may also accept information other than user identifiers. For example, the accepting unit 13 may accept an instruction to acquire a captured image.

For example, the accepting unit 13 may accept information input from an input device (e.g., a keyboard, a mouse, a touch panel, etc.), receive information transmitted via a wired or wireless communication line, or accept information read from a predetermined storage medium (e.g., an optical disk, a magnetic disk, a semiconductor memory, etc.). The accepting unit 13 may or may not include a device that accepts information (e.g., a modem, a network card, etc.). The accepting unit 13 may be realized by hardware, or software such as a driver that drives a predetermined device.

The time and date information acquiring unit 14 acquires time and date information indicating a time and date at which the captured image was captured. The time and date information may indicate accurate time and date at which the image was captured, or approximate time and date at which the image was captured. For example, the time and date information acquiring unit 14 may acquire time and date information from the captured image, or acquire time and date information from an unshown calendar unit or clock unit. In the case of the former, the header of the captured image or the like may contain the time and date at which the image was captured, and the time and date information acquiring unit 14 may acquire time and date information indicating the time and date at which the image was captured, by reading it from the captured image. In the case in which the time and date information is acquired from the calendar unit or the like, it is preferable to acquire the time and date information such that the point in time at which the captured image acquiring unit 11 acquired the captured image is close to the point in time at which the time and date information was acquired. In this embodiment, the case in which the time and date information acquiring unit 14 acquires time and date information from an unshown calendar unit or clock unit will be mainly described.

The output unit 15 outputs the score calculated by the calculating unit 12. The output may be, for example, display on a display device (e.g., a liquid crystal display, etc.), transmission via a communication line to a predetermined device, printing by a printer, sound output by a speaker, accumulation in a storage medium, or delivery to another constituent element. The output unit 15 may or may not include a device that performs output (e.g., a display device, a printer, etc.). The output unit 15 may be realized by hardware, or software such as a driver that drives these devices. In this embodiment, the case in which the output unit 15 transmits a score to a server (not shown) will be mainly described. The output unit 15 may transmit the score, the user identifier accepted by the accepting unit 13, and the time and date information acquired by the time and date information acquiring unit 14, in association with each other, to the server. The server is a server that manages a score for each user. The server may receive similar information from two or more hygiene evaluation apparatuses 1.

Next, an operation of the hygiene evaluation apparatus 1 will be described with reference to the flowchart in FIG. 2.

(Step S101) The accepting unit 13 determines whether or not it has accepted a user identifier. Then, if it has accepted a user identifier, the procedure advances to step S102, or otherwise the processing in step S101 is repeated until a user identifier is accepted.

(Step S102) The captured image acquiring unit 11 acquires a captured image of a hand of a user identified with the user identifier accepted in step S101. For example, the captured image acquiring unit 11 may acquire multiple captured images corresponding to both sides of both hands of the user.

(Step S103) The calculating unit 12 calculates a score regarding the substance stuck to the hand, using the captured image acquired in step S102. If multiple captured images corresponding to one examinee are acquired in step S102, the score may be calculated using the multiple captured images.

(Step S104) The time and date information acquiring unit 14 acquires time and date information indicating the time and date at that point in time, from an unshown calendar unit or clock unit.

(Step S105) The output unit 15 transmits the user identifier acquired in step S101, the score acquired in step S103, and the time and date information acquired in step S104, in association with each other, to a server. Then, the procedure returns to step S101.

Figure 2:
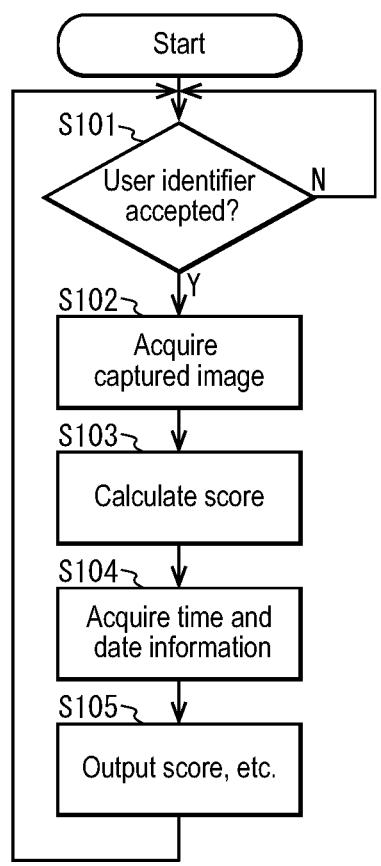
FIG. 2 is a flowchart showing an operation of the hygiene evaluation apparatus according to the embodiment.

Note that the processing order in the flowchart in FIG. 2 is merely an example, and the order in the steps may be changed as long as similar results can be obtained. In the flowchart in FIG. 2, the processing is ended when the apparatus is turned off or at an interruption of termination processing.

Next, an operation of the hygiene evaluation apparatus 1 according to this embodiment will be described by way of a specific example. In this specific example, the case in which handwashing is evaluated as in (1) above will be described. In this specific example, it is assumed that the score is incremented by 1 if the fluorescent substance remains in a half or more the area of each of the 72 portions of both hands. Accordingly, the score is any value of 0 to 72, where the lower the score, the better the hygiene state (i.e., the more proper the handwashing).

Figure 4:
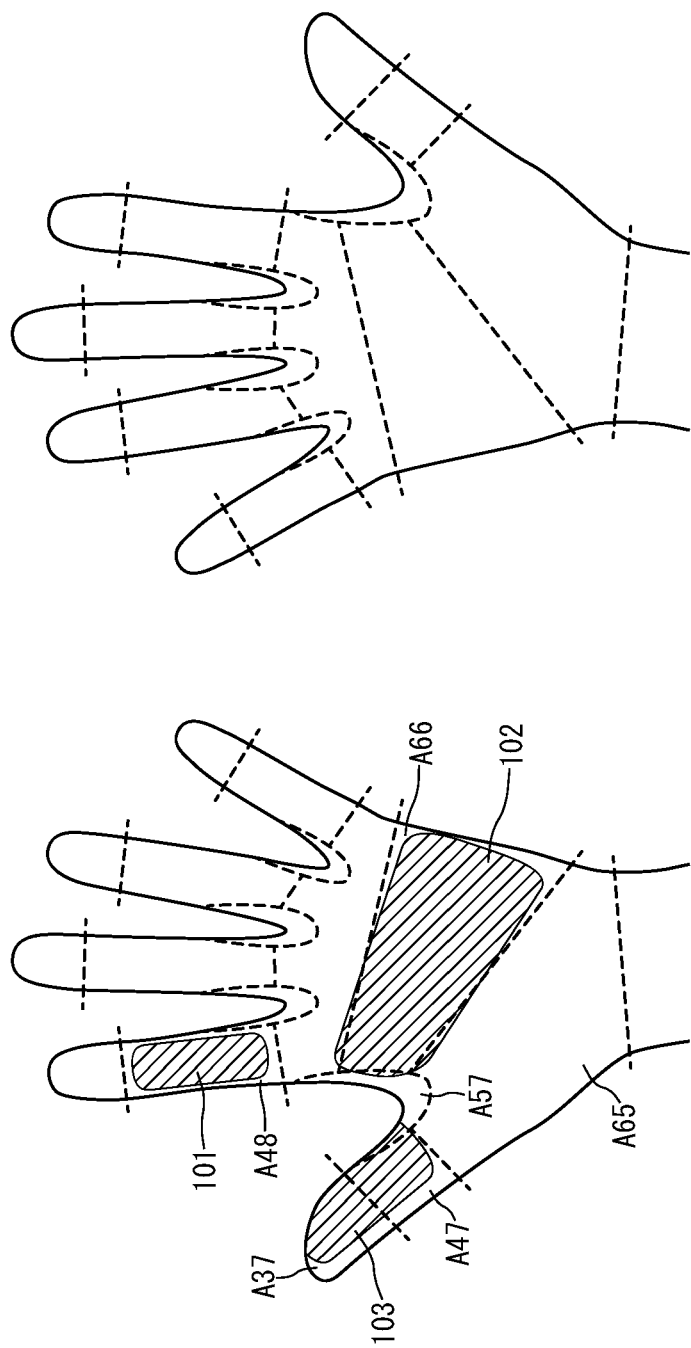
FIG. 4 is a diagram showing an example of a captured image of hands according to the embodiment.

First, it is assumed that a user identified with a user identifier "U001" (hereinafter, also referred to as a "user U001": the same applies to the other users) uniformly rubs a lotion containing a fluorescent substance into both sides of his or her hands before handwashing, and then washes the hands. Then, it is assumed that the user U001 inputs his or her user identifier "U001" by operating the hygiene evaluation apparatus 1. Then, the user identifier is accepted by the accepting unit 13 and delivered to the output unit 15 (step S101). Subsequently, when the user U001 puts the palm side of the hands into the image capturing region of the image capturing apparatus 7, the captured image acquiring unit 11 detects this event, and acquires the captured image shown in FIG. 4. The image capturing region is irradiated with ultraviolet light from the light source 6 that is a black light device. In the captured image in FIG. 4, the broken lines indicating the boundaries between the portions are added for the sake of description, and are not included in the captured image. The shaded regions 101 to 103 are fluorescent regions. Subsequently, when the user U001 puts the back side of the hands into the image capturing region in a similar manner, a captured image is again acquired in response to that event (step S102). In this manner, captured images of both sides of both hands of the user U001 are acquired.

Next, the calculating unit 12 sets the score to 0, which is an initial value. A half or more the area of each of the portions A37, A47, A48, and A66 has a fluorescent region in the captured image of the palm side in FIG. 4, and thus the calculating unit 12 increments the score by 4. Some of the portions such as A57 and A65 in the captured image in FIG. 4 each have a fluorescent region, but the area of the fluorescent region is not a half or more the area of the portion, and thus the counting of the score is not performed for these portions. It is assumed that two portions each have a fluorescent region in a half or more the area thereof, in the captured image of the back side. Then, the calculating unit 12 increments the score by 2, and delivers the score "6", which is the sum of the results, to the output unit 15 (step S103).

Upon receipt of the user identifier and the score, the output unit 15 delivers an instruction to acquire time and date information, to the time and date information acquiring unit 14. Upon receipt of the instruction, the time and date information acquiring unit 14 acquires time and date information indicating the time and date at that point in time from an unshown calendar unit and clock unit, and delivers it to the output unit 15 (step S104). It is assumed that the time and date indicated by the time and date information is 9:15, Jul. 3, 2017. Upon receipt of the time and date information, the output unit 15 transmits a packet containing the user identifier "U001", the score "6", and the time and date information "9:15, Jul. 3, 2017" to an address of a preset server (step S105). The packet is received by the unshown server, and accumulated in a storage medium in such a manner that the user identifier, the time and date information, and the score are associated with each other.

Figure 6:
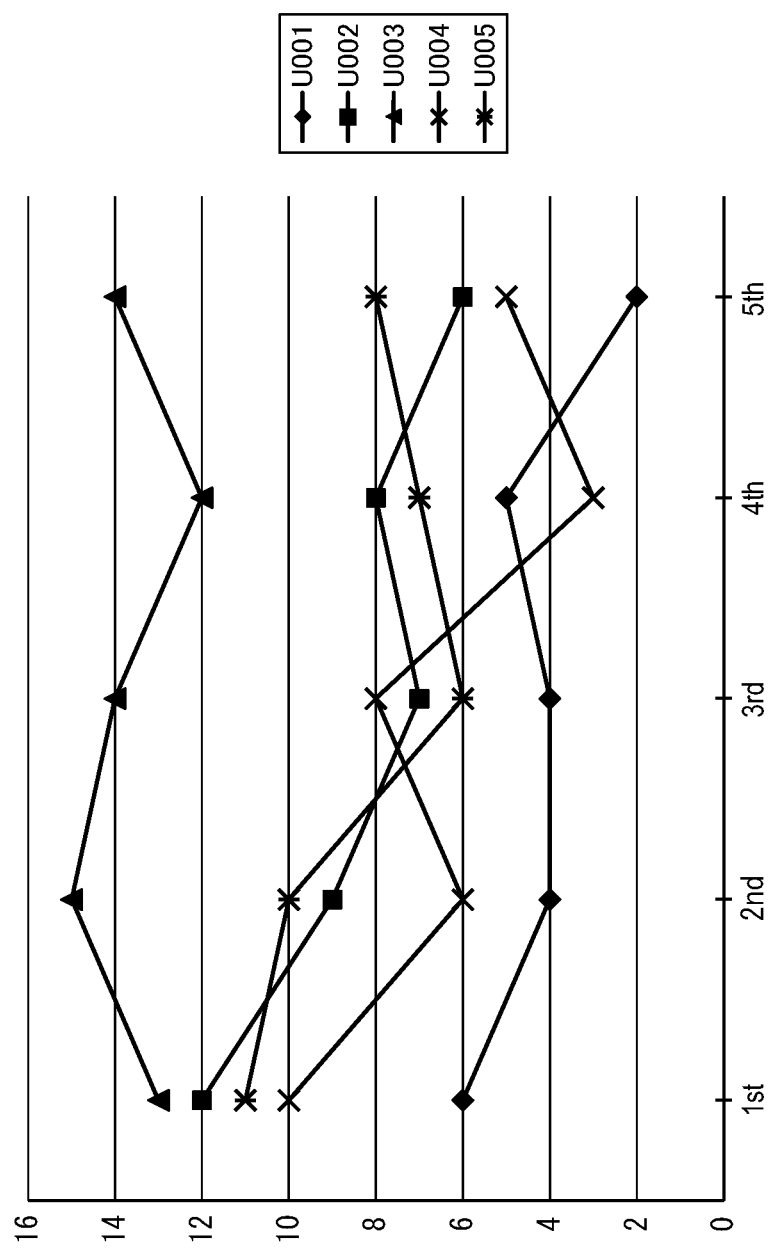
FIG. 6 is a graph showing an example of a change in the score for each user according to the embodiment.

Subsequently, similar processing is repeated for other users as well, and the scores after handwashing are transmitted to the server in association with the user identifiers and the like. It is assumed that the scores after handwashing of the user U001 and the like are transmitted to the server on July 4 and thereafter as well. As a result, the user identifiers and the like stored in the server are as shown in FIG. 5. Subsequently, the user U001 or the like can see a change in the scores of the users and the like, by accessing the server through operation of an information processing apparatus or the like. For example, the server may output the graph shown in FIG. 6, according to the scores and the like shown in FIG. 5. If the graph in FIG. 6 is output, it is possible to see a change in the hygiene states of the users. For example, the scores of the user U003 are successively higher than those of the other users, and thus it is possible to urge the user to perform handwashing more carefully.

As described above, with the hygiene evaluation apparatus 1 according to this embodiment, a score regarding a hygiene state of a hand of an examinee can be acquired using a captured image of the hand. The score is a score regarding a substance stuck to the hand, and thus the hygiene state of the hand can be evaluated not indirectly but directly, and the evaluation can be performed more accurately. Since a user identifier, a score, and time and date information are transmitted to a server, scores for respective users can be managed in the server for each point in time and date. Accordingly, hygiene states of hands of users can be seen in time series, and thus a user whose handwashing or hand sanitization continues to be inadequate can be urged to perform them properly, and a user whose handwashing or the like continues to be proper can be commended for that act. Furthermore, a game element can be introduced into the improvement of a hygiene state of hands by comparing hygiene states of hands of multiple users, and examinees can improve the hygiene states of hands through competition with other examinees.

In this embodiment, the case was mainly described in which the output unit 15 transmits a score, a user identifier, and time and date information, in association with each other, to a server, but there is no limitation to this. The output unit 15 may display or accumulate these types of information.

Also, in this embodiment, the case was described in which the hygiene evaluation apparatus 1 includes the time and date information acquiring unit 14, but it is also possible that the hygiene evaluation apparatus 1 does not include the time and date information acquiring unit 14. In that case, the output unit 15 may output a user identifier and a score in association with each other.

Also, in this embodiment, the case was mainly described in which the output unit 15 outputs a user identifier accepted by the accepting unit 13 and a score in association with each other, but there is no limitation to this. The output unit 15 may display or print a score calculated by the calculating unit 12. In that case, it is also possible that the hygiene evaluation apparatus 1 does not include the accepting unit 13 that accepts a user identifier.

Embodiment 2

Hereinafter, a hygiene evaluation apparatus according to Embodiment 2 of the present invention will be described with reference to the drawings. The hygiene evaluation apparatus according to this embodiment performs statistical processing on a score for each user.

Figure 7:
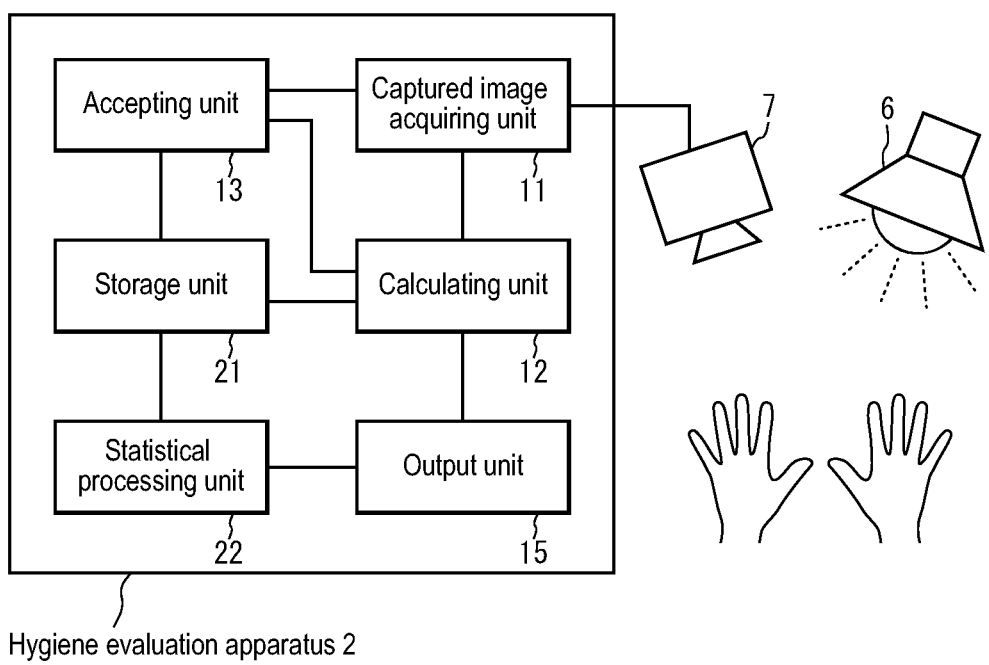
FIG. 7 is a block diagram showing the configuration of a hygiene evaluation apparatus according to Embodiment 2 of the present invention.

FIG. 7 is a block diagram showing the configuration of a hygiene evaluation apparatus 2 according to this embodiment. The hygiene evaluation apparatus 2 according to this embodiment includes the captured image acquiring unit 11, the calculating unit 12, the accepting unit 13, the output unit 15, a storage unit 21, and a statistical processing unit 22. The configurations and operations of those other than the storage unit 21 and the statistical processing unit 22 are as described in Embodiment 1 unless otherwise described below, and thus a detailed description thereof has been omitted. It is assumed that a user identifier accepted by the accepting unit 13 and a score of a user identified with the user identifier, the score being calculated by the calculating unit 12, are accumulated in association with each other in the storage unit 21. The output unit 15 outputs a result of statistical processing as well.

As described above, it is assumed that, for each user, a user identifier and a score are stored in association with each other in the storage unit 21. In the storage unit 21, information may be temporarily stored in a RAM or the like, or may be stored for a long period of time. The storage unit 21 may be realized by a predetermined storage medium (e.g., a semiconductor memory, a magnetic disk, etc.).

The statistical processing unit 22 performs statistical processing on scores respectively corresponding to multiple users identified with multiple user identifiers accepted by the accepting unit 13. Specifically, the statistical processing unit 22 may read multiple scores respectively corresponding to multiple users from the storage unit 21, and perform statistical processing on the read multiple scores. The statistical processing may be, for example, acquiring a representative value, calculation of a value regarding data distribution, or other types of statistical processing. The representative value may be, for example, an average or a median. The value regarding data distribution may be, for example, variance or standard deviation. For example, the statistical processing unit 22 may perform statistical processing, using latest scores of the respective users. The score that is subjected to statistical processing may be, for example, a score with in a predetermined period of time (e.g., within the last one week, etc.). In that case, the hygiene evaluation apparatus 2 may have the time and date information acquiring unit 14. Then, the score may be stored in the storage unit 21 in association with the time and date information acquired by the time and date information acquiring unit 14. The average or the like obtained as a result of the statistical processing is also output by the output unit 15. The result of the statistical processing may be output together with, or separately from, the score calculated by the calculating unit 12.

Next, an operation of the hygiene evaluation apparatus 2 will be described with reference to the flowchart in FIG. 8. In the flowchart in FIG. 8, the processing in steps S101 to S103 is similar to that in the flowchart in FIG. 2, and thus a description thereof has been omitted. It is assumed that, in step S101, if the accepted user identifier is not stored in the storage unit 21, the accepting unit 13 accumulates the user identifier in the storage unit 21.

(Step S201) The calculating unit 12 accumulates the score calculated in step S103 in the storage unit 21 in association with the user identifier accepted in step S101. The user identifier accepted in step S101 has been already stored in the storage unit 21, and thus it is assumed that the calculating unit 12 accumulates the calculated score in the storage unit 21 such that the correspondence between the score and the user identifier is known. If a score corresponding to the user identifier has been already accumulated, the calculating unit 12 may accumulate a new score through overwriting or accumulate a new score separately from the previous score. Even in the case of the latter, it is preferable to perform accumulation such that the lastly accumulated score can be specified.

(Step S202) The statistical processing unit 22 performs statistical processing, using the score for each user identifier stored in the storage unit 21. The statistical processing is preferably performed using the latest score, that is, the lastly accumulated score corresponding to each user identifier. The result of the statistical processing may also be stored in the storage unit 21.

(Step S203) The output unit 15 outputs the score calculated by the calculating unit 12 and the result of the statistical processing by the statistical processing unit 22. Then, the procedure returns to step S101. The output may be, for example, display to a user or the like.

Figure 8:
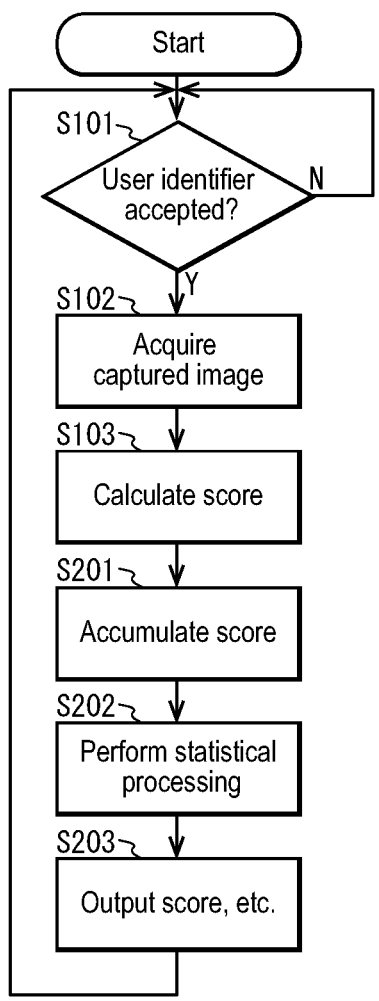
FIG. 8 is a flowchart showing an operation of the hygiene evaluation apparatus according to the embodiment.

Note that the processing order in the flowchart in FIG. 8 is merely an example, and the order in the steps may be changed as long as similar results can be obtained. In the flowchart in FIG. 8, the processing is ended when the apparatus is turned off or at an interruption of termination processing.

As described above, with the hygiene evaluation apparatus 2 according to this embodiment, the user can see a result of the statistical processing as well. For example, if the statistical processing is calculation of an average, the user can see the average and his or her own score, and see whether or not the handwashing or sanitization state is better than the average. As a result, it is possible to prompt the user to improve the hygiene state of the hands.

Embodiment 3

Hereinafter, a hygiene evaluation image capturing system according to Embodiment 3 of the present invention will be described with reference to the drawings. The hygiene evaluation image capturing system according to this embodiment includes a hygiene evaluation apparatus, and an image capturing mount on which the hygiene evaluation apparatus can be mounted.

Figure 9:
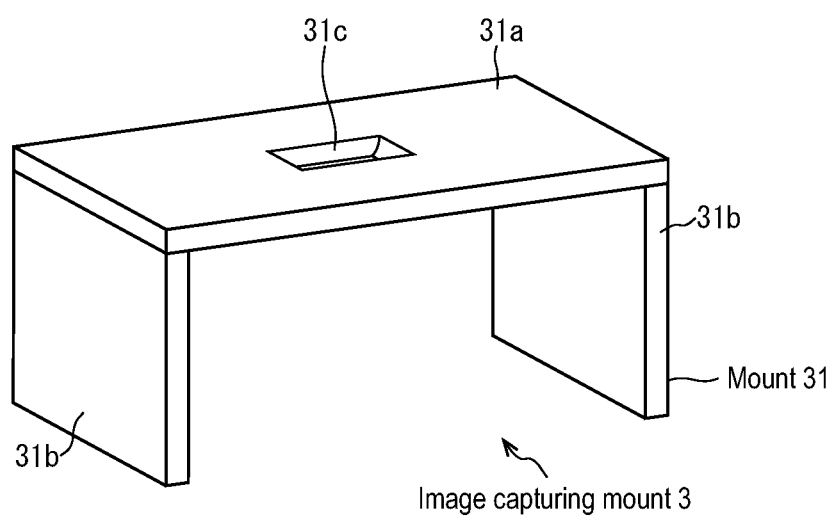
FIG. 9 is a perspective view showing an image capturing mount according to Embodiment 3 of the present invention.
Figure 10:
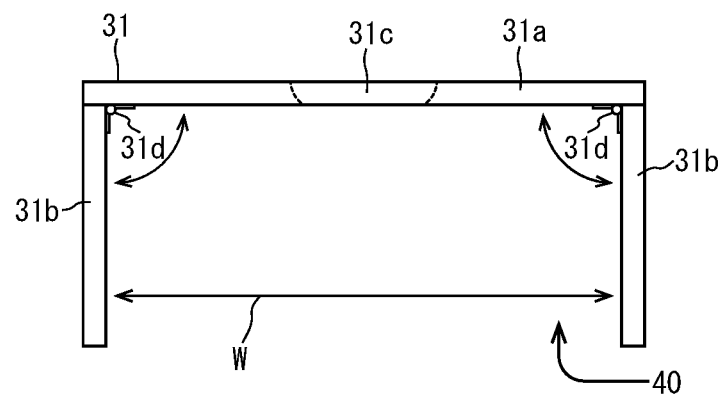
FIG. 10 is a front view showing the image capturing mount according to the embodiment.
Figure 11:
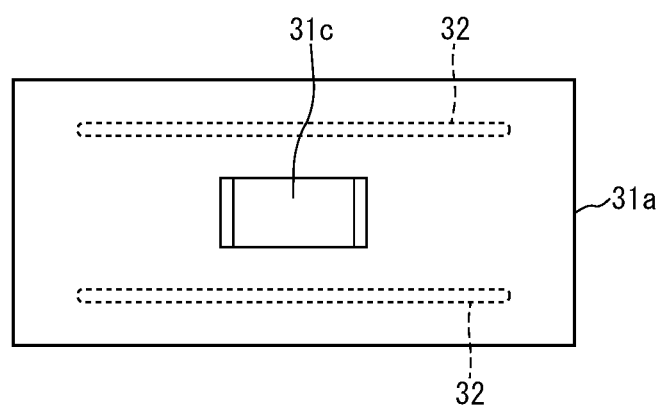
FIG. 11 is a top view showing the image capturing mount according to the embodiment.
Figure 12:
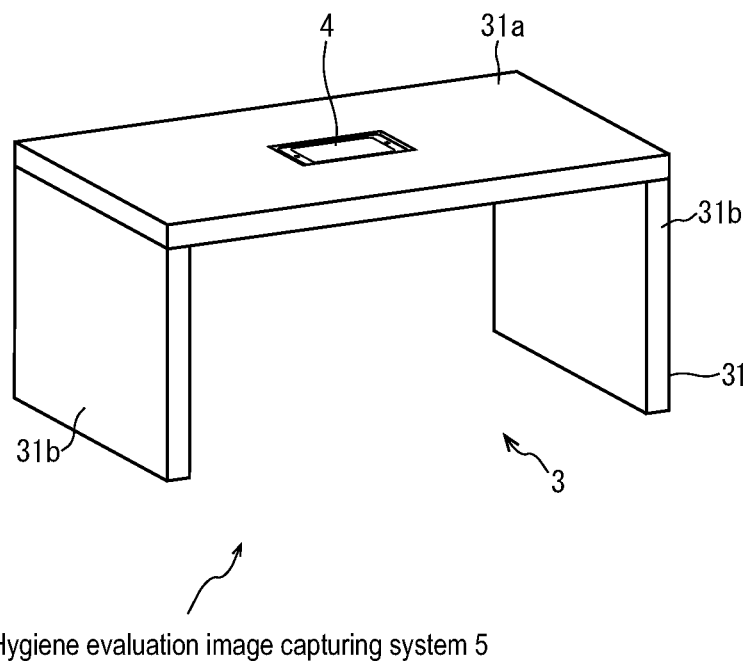
FIG. 12 is a perspective view showing a hygiene evaluation image capturing system including an image capturing mount and a hygiene evaluation apparatus according to the embodiment.

FIG. 9 is a perspective view of an image capturing mount 3 according to this embodiment, FIG. 10 is a front view of the image capturing mount 3, and FIG. 11 is a top view of the image capturing mount 3. FIG. 12 is a perspective view of a hygiene evaluation image capturing system 5 according to this embodiment.

The hygiene evaluation image capturing system 5 according to this embodiment includes the image capturing mount 3 and a hygiene evaluation apparatus 4. The image capturing mount 3 is a mount on which the hygiene evaluation apparatus 4 is detachably mounted, and includes a mount 31, and light sources 32 provided on the mount 31. The hygiene evaluation apparatus 4 according to this embodiment is a portable information terminal that can be carried around. The portable information terminal may be, for example, a smartphone, a tablet, a PDA (personal digital assistant), or the like. The configurations and operations of the hygiene evaluation apparatus 4 are similar to those of the hygiene evaluation apparatuses 1 and 2 according to Embodiments 1 and 2, and thus a detailed description thereof has been omitted. The captured image acquiring unit 11 of the hygiene evaluation apparatus 4 captures an image. Accordingly, it is assumed that a portable information terminal serving as the hygiene evaluation apparatus 4 has an image capturing function.

The mount 31 includes a stage portion 31a on which the hygiene evaluation apparatus 4 is mounted, and leg portions 31b attached to the stage portion 31a. The stage portion 31a has an opening 31c, and the hygiene evaluation apparatus 4 that is a portable information terminal can be detachably mounted into the opening 31c. In this embodiment, it is assumed that the area of the opening 31c on the lower face side of the stage portion 31a is smaller than that of the opening 31c on the upper face side, the area of the opening 31c on the upper face of the stage portion 31a is larger than that in the planar direction of the hygiene evaluation apparatus 4, and the area of the opening 31c on the lower face of the stage portion 31a is smaller than that in the planar direction of the hygiene evaluation apparatus 4. Accordingly, as shown in FIG. 12, when the hygiene evaluation apparatus 4 is placed into the opening 31c from above, the hygiene evaluation apparatus 4 can be mounted on the stage portion 31a. It will be appreciated that the hygiene evaluation apparatus 4 may be mounted on the stage portion 31a using other methods.

As shown in FIG. 10, the two leg portions 31b are foldably attached to the stage portion 31a respectively via hinges 31d. Accordingly, when the mount 31 is carried or accommodated, for example, the portability and the accommodatability can be increased by folding the leg portions 31b. There is no limitation on the number of leg portions 31b. The number of leg portions 31b may be one, or three or more.

Furthermore, a hand image capturing space 40 defined by the stage portion 31a and the leg portions 31b may have a size that allows the captured image acquiring unit 11 to capture images of both hands simultaneously. Accordingly, for example, in FIG. 10, a width W between the two leg portions 31b may be larger than the width of two hands, such as 30 cm or more or 40 cm or more.

As shown in FIG. 11, the light sources 32 are linearly provided along two sides of the opening 31c on the lower face side of the stage portion 31a. The light sources 32 are arranged so as to irradiate the image capturing space 40 with light, and may be, for example, black light devices, ultraviolet light LEDs, or light sources that emit light with other wavelengths. It is assumed that the captured image acquiring unit 11 of the hygiene evaluation apparatus 4 acquires a captured image, by capturing an image of a hand irradiated with light from the light sources 32.

Next, a specific method for evaluating a hygiene state using the hygiene evaluation image capturing system 5 according to this embodiment will be briefly described.

First, as shown in FIG. 12, a user mounts the hygiene evaluation apparatus 4 that is a smartphone, into the opening 31c of the stage portion 31a, and turns on the light sources 32. Subsequently, as with the specific example of Embodiment 1, the user rubs a lotion containing a fluorescent substance into his or her hands, washes the hands, and then places the hands after the handwashing into the image capturing space 40. Upon detection of the shape of hands, the captured image acquiring unit 11 of the hygiene evaluation apparatus 4 accordingly captures an image thereof, thereby acquiring the captured image. Subsequently, when the user changes the sides of the hands and then places the hands again into the image capturing space 40, an image thereof is again captured accordingly, and thus the captured image is acquired. The following processing for acquiring scores, and outputting the scores and the like is similar that in Embodiments 1 and 2, and thus a detailed description thereof has been omitted. The scores and the like may be, for example, displayed on a touch panel of the hygiene evaluation apparatus 4, or transmitted from the hygiene evaluation apparatus 4 to the server.

As described above, with the hygiene evaluation image capturing system 5 according to this embodiment, it is easy to perform hygiene evaluation using the image capturing mount 3 and the hygiene evaluation apparatus 4 that is a smartphone or the like. It seems that, in particular, since hygiene evaluation can be performed using smartphones or the like of users, the hygiene evaluation is made easier to perform, and the hygiene state of hands of a larger number of users can be improved.

In this embodiment, the case was described in which the leg portions 31b are foldable, but there is no limitation to this. If the portability and the accommodatability are not required for the mount 31, it is also possible that the leg portions 31b are not foldable, that is, are fixed to the stage portion 31a.

Also, in this embodiment, the case was described in which images of both hands can be simultaneously captured in the image capturing space 40, but there is no limitation to this. For example, if the mount 31 is required to be smaller, the image capturing space 40 may have a size that allows only one hand to be placed therein.

Furthermore, in this embodiment, the hygiene evaluation apparatus 4 and the light sources 32 may be controlled so as to operate in conjunction with each other such that the light sources 32 are turned on only when an image of a hand is captured. In that case, for example, the hygiene evaluation apparatus 4 and the light sources 32 may be connected to each other via a wire or wirelessly (e.g., Wi-Fi, Bluetooth (registered trademark), etc.), and an instruction to be turned on may be transmitted from the hygiene evaluation apparatus 4 to the light sources 32 only when the captured image acquiring unit 11 acquires a captured image. The light sources 32 may be turned on according to the instruction to be turned on, only when an image of a hand is captured.

Furthermore, in the foregoing embodiments, the captured image acquiring unit 11 may acquire a captured image only when light is emitted from the light source(s) 6 or 32. For example, the captured image acquiring unit 11 may determine whether or not the light source(s) 6 or 32 are on, based on detection of the brightness in the image capturing region, detection of light with a predetermined wavelength, or the like, and acquire a captured image only when it is determined that the light source(s) are on.

Furthermore, in the foregoing embodiments, the case was described in which a hand into which a specific substance was rubbed or a hand into which a sanitizer containing a specific substance was rubbed was subjected to image capturing, but there is no limitation to this. It is also possible that a hand into which a specific substance or a sanitizer has not been rubbed may be subjected to image capturing. In that case, the substance stuck to the hand subjected to score calculation by the calculating unit 12 may be, for example, dirt stuck to the hand. The dirt may be, for example, mud, grease, blood, or the like. In this case, for example, the calculating unit 12 may detect a region of a substance (dirt) stuck to the hand, by detecting a region with a color different from that of the hand, or may detect a region of a substance (dirt) stuck to the hand, by detecting a region with a color that matches the color of dirt registered in advance. In the case of the latter, for example, a score may be calculated for each type of dirt. Specifically, a score of mud, a score of grease, a score of blood, and the like may be calculated. In this case, a score indicating a less degree to which a substance is stuck to the hand means a better hygiene state.

Furthermore, in Embodiments 1 and 2 above, the case was described in which the hygiene evaluation apparatuses 1 and 2 are stand-alone apparatuses, but the hygiene evaluation apparatuses 1 and 2 may be either stand-alone apparatuses, or server apparatuses in a server-client system. In the case of the latter, the captured image acquiring unit, the accepting unit, and the output unit may acquire a captured image, accept information, or output information, via a communication line.

Furthermore, in the foregoing embodiments, each process or each function may be realized as centralized processing using a single apparatus or a single system, or may be realized as distributed processing using multiple apparatuses or multiple systems.

Furthermore, in the foregoing embodiments, information transmission performed between constituent elements may be such that, for example, if two constituent elements for transmitting information are physically different from each other, the transmission is performed by one of the constituent elements outputting the information and the other constituent element accepting the information, or alternatively, if two constituent elements for transmitting information are physically the same, the transmission is performed by shifting from a processing phase corresponding to one of the constituent elements to a processing phase corresponding to the other constituent element.

Furthermore, in the foregoing embodiments, information related to the processing that is performed by each constituent element, for example, information that is accepted, acquired, selected, generated, transmitted, or received by each constituent element, information such as a threshold value, a numerical expression, or an address used by each constituent element in the processing, and the like may be retained in an unshown storage medium temporarily or for a long period of time even if not specified in the description above. Furthermore, the information may be accumulated in the unshown storage medium by each constituent element or by an unshown accumulating unit. Furthermore, the information may be read from the unshown storage medium by each constituent element or by an unshown reading unit.

Furthermore, in the foregoing embodiments, if information used by each constituent element or the like, for example, information such as a threshold value, an address, or various setting values used by each constituent element in the processing may be changed by a user, the user may or may not be allowed to change such information as appropriate even if not specified in the description above. If the user is allowed to change such information, the change may be realized by, for example, an unshown accepting unit that accepts a change instruction from the user and an unshown changing unit that changes information according to the change instruction. The accepting the change instruction by the unshown accepting unit may be, for example, accepting the information from an input device, receiving the information transmitted via a communication line, or accepting the information read from a predetermined storage medium.

Furthermore, in the foregoing embodiments, if two or more constituent elements included in the hygiene evaluation apparatuses 1, 2, and 4 have a communication device, an input device, or the like, the two or more constituent elements may have a physically single device, or may have different devices.

Furthermore, in the foregoing embodiments, each constituent element may be constituted by dedicated hardware, or alternatively, constituent elements that can be realized by software may be realized by executing a program. For example, each constituent element may be realized by a program execution unit such as a CPU reading and executing a software program stored in a storage medium such as a hard disk or a semiconductor memory. At the time of executing the program, the program execution unit may execute the program while accessing the storage unit or the storage medium. Software that realizes the hygiene evaluation apparatuses 1, 2, and 4 according to the foregoing embodiments is a program as follows. Specifically, this program is a program for causing a computer to execute: a captured image acquiring step of acquiring a captured image of a hand; a calculating step of calculating a score regarding a substance stuck to the hand, using the captured image; and an output step of outputting the score calculated in the calculating step.

In the above-described program, the functions realized by the program do not include a function that can be realized only by hardware. For example, the functions of a modem, an interface card, and so on employed in an acquiring step of acquiring information or an output step of outputting information, and so on, which can be realized only by hardware, are at least not included in the functions realized by the above-described program.

Furthermore, this program may be executed by downloading from a server or the like, or may be executed by reading a program stored in a predetermined storage medium (e.g., an optical disk such as a CD-ROM, a magnetic disk, a semiconductor memory, etc.). Furthermore, the program may be used as a program for constituting a program product.

Furthermore, a computer that executes the program may be a single computer or may be multiple computers. That is to say, centralized processing may be performed, or distributed processing may be performed.

Figure 13:
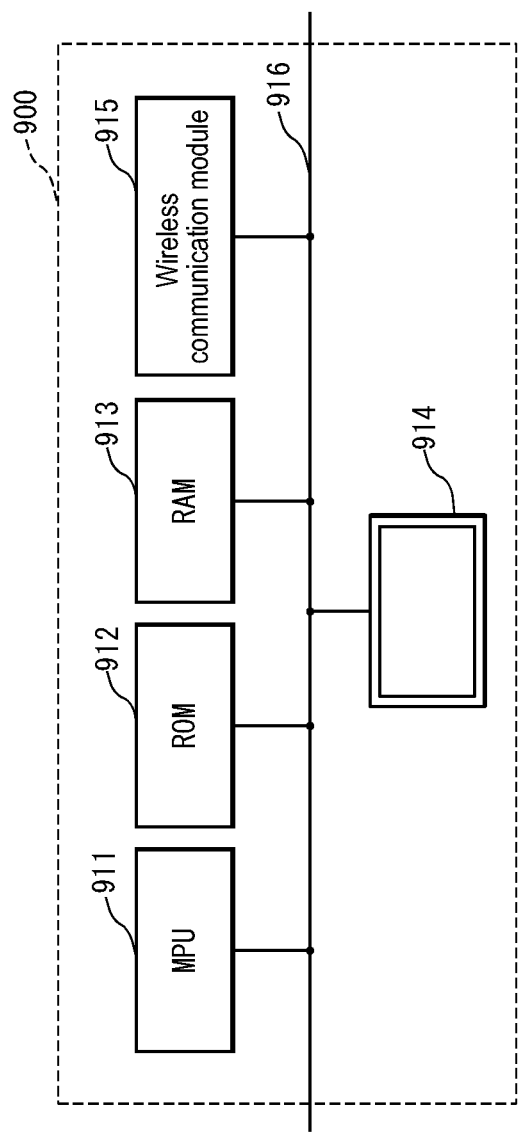
FIG. 13 is diagram showing an example of the configuration of a computer system according to the embodiments above.

FIG. 13 is a diagram showing an example of a computer system 900 that executes the above-described program to realize the hygiene evaluation apparatuses 1, 2, and 4 according to the foregoing embodiments. The foregoing embodiments may be realized using computer hardware and computer programs executed thereon.

In FIG. 13, the computer system 900 includes an MPU (micro processing unit) 911, a ROM 912 such as a flash memory in which a program such as a boot up program, an application program, a system program, and data are to be stored, an RAM 913 that is connected to the MPU 911 and in which a command of an application program is temporarily stored and a temporary storage area is provided, a touch panel 914, a wireless communication module 915, and a bus 916 that connects the MPU 911, the ROM 912, and the like. Instead of the wireless communication module 915, a wired communication module may be included. Instead of the touch panel 914, an input device constituted by a display screen, and a mouse, a keyboard, or the like may be included.

The program for causing the computer system 900 to execute the functions of the hygiene evaluation apparatuses 1, 2, and 4 according to the foregoing embodiments may be stored in the ROM 912 via the wireless communication module 915. The program is loaded into the RAM 913 at the time of execution. The program may be loaded directly from a network.

The program does not necessarily have to include, for example, an operating system (OS) or a third party program to cause the computer system 900 to execute the functions of the hygiene evaluation apparatuses 1, 2, and 4 according to the foregoing embodiments. The program may only include a command portion to call an appropriate function or module in a controlled mode and obtain desired results. The manner in which the computer system 900 operates is well known, and thus a detailed description thereof has been omitted.

The present invention is not limited to the embodiments set forth herein. Various modifications are possible within the scope of the present invention.

As described above, the hygiene evaluation apparatus and the like according to the present invention have an effect that a hygiene state of hands can be precisely evaluated, and thus they are useful, for example, as hygiene evaluation apparatuses for hands and the like for use in training of healthcare workers and for preventing infection.

The invention claimed is:

1. A hygiene evaluation apparatus comprising:
a captured image acquiring unit that acquires a captured image of a hand;
a calculating unit that specifies, in a hand image contained in the captured image, regions corresponding to predetermined multiple portions of the hand, determines whether or not a substance is stuck to each of the predetermined multiple portions, using the captured image, and calculates a score according to the determined results; and
an output unit that outputs the score calculated by the calculating unit,
wherein the hand is divided into the predetermined multiple portions such that a portion in which it is important to improve a hygiene state has a small area, and a portion in which it is not important to improve the hygiene state has a large area.

2. The hygiene evaluation apparatus according to claim 1, wherein the score is a value regarding a degree to which a substance that has not been removed through handwashing remains on the hand.

3. The hygiene evaluation apparatus according to claim 1, wherein the score is a value regarding a degree to which a substance contained in a sanitizer is stuck to the hand.

4. The hygiene evaluation apparatus according to claim 1, further comprising an accepting unit that accepts a user identifier for identifying a user subjected to image capturing,
wherein the output unit outputs the score and the user identifier accepted by the accepting unit in association with each other.

5. The hygiene evaluation apparatus according to claim 4, further comprising a time and date information acquiring unit that acquires time and date information indicating a time and date at which the captured image was captured,
wherein the output unit outputs the score, the user identifier, and the time and date information acquired by the time and date information acquiring unit, in association with each other.

6. The hygiene evaluation apparatus according to claim 1, further comprising:
an accepting unit that accepts a user identifier for identifying a user subjected to image capturing; and
a statistical processing unit that performs statistical processing on scores respectively corresponding to multiple users identified with multiple user identifiers accepted by the accepting unit,
wherein the output unit outputs a result of the statistical processing as well.

7. An image capturing mount comprising:
a mount on which the hygiene evaluation apparatus according to claim 1 is detachably mounted; and
a light source provided on the mount,
wherein the captured image acquiring unit acquires the captured image, by capturing an image of a hand irradiated with light from the light source.

8. The image capturing mount according to claim 7,
wherein the mount includes a stage portion on which the hygiene evaluation apparatus is mounted, and a leg portion attached to the stage portion, and
a hand image capturing space defined by the stage portion and the leg portion has a size that allows the captured image acquiring unit to capture images of both hands simultaneously.

9. The image capturing mount according to claim 8, wherein the leg portion is foldably attached to the stage portion.

10. A hygiene evaluation image capturing system comprising:
the image capturing mount according to claim 9; and
the hygiene evaluation apparatus mounted on the mount.

11. A hygiene evaluation method comprising:
a captured image acquiring step of acquiring a captured image of a hand;
a specifying step of specifying, in a hand image contained in the captured image, regions corresponding to predetermined multiple portions of the hand;
a determining step of determining whether or not a substance is stuck to each of the predetermined multiple portions, using the captured image;
a calculating step of calculating a score according to the determined results; and
an output step of outputting the score calculated in the calculating step,
wherein the hand is divided into the predetermined multiple portions such that a portion in which it is important to improve a hygiene state has a small area, and a portion in which it is not important to improve the hygiene state has a large area.

12. A program for causing a computer to execute:
a captured image acquiring step of acquiring a captured image of a hand;

a specifying step of specifying, in a hand image contained in the captured image, regions corresponding to predetermined multiple portions of the hand;

a determining step of determining whether or not a substance is stuck to each of the predetermined multiple portions, using the captured image;

a calculating step of calculating a score according to the determined results; and an output step of outputting the score calculated in the calculating step, wherein the hand is divided into the predetermined multiple portions such that a portion in which it is important to improve a hygiene state has a small area, and a portion in which it is not important to improve the hygiene state has a large area.

13. The hygiene evaluation apparatus according to claim 1, wherein the calculating unit determines whether or not a substance is stuck to a portion, by comparing a proportion of an area of a region to which the substance is stuck with respect to an area of the portion, and a threshold.

\* \* \* \* \*